(12) United States Patent
Barney et al.

(10) Patent No.: US 6,326,185 B1
(45) Date of Patent: Dec. 4, 2001

(54) METHOD FOR DECONTAMINATING YEAST

(75) Inventors: Michael C. Barney, Elm Grove; Kathleen M. Carrick, Racine; Alfonso Navarro, Milwaukee; David S. Ryder, Mequon, all of WI (US)

(73) Assignee: Miller Brewing Company, Milwaukee, WI (US)

( * ) Notice: Subject to any disclaimer, the term of this patent is extended or adjusted under 35 U.S.C. 154(b) by 0 days.

(21) Appl. No.: 09/553,775

(22) Filed: Apr. 21, 2000

Related U.S. Application Data (60) Provisional application No. 60/130,591, filed on Apr. 22, 1999.

(51) Int. Cl.[7] ................ C12N 1/16; C12N 1/18
(52) U.S. Cl. .................. 435/255.1; 435/255.2; 435/255.21; 435/256.18; 426/11
(58) Field of Search ............... 435/255.1, 255.2, 435/256.8, 255.21; 426/11

(56) References Cited

U.S. PATENT DOCUMENTS

| | | | |
|---|---|---|---|
| 1,449,111 | 3/1923 | Hayduck . | |
| 5,082,975 | 1/1992 | Todd, Jr. et al. | 568/315 |
| 5,166,449 | 11/1992 | Todd, Jr. et al. | 568/377 |
| 5,286,506 | 2/1994 | Millis et al. | 426/355 |
| 5,370,863 | 12/1994 | Barney et al. | 424/49 |

FOREIGN PATENT DOCUMENTS

| | | | |
|---|---|---|---|
| WO 97/33971 | 9/1997 | (WO) | C12C/3/00 |
| WO 00/52212 | 9/2000 | (WO) | C13D/1/00 |

OTHER PUBLICATIONS

Schmalreck, et al., "Structural features determining the antibiotic potencies of natural and synthetic hop bitter resins, their precursors and derivatives," *Can. J. Microbiol.* 21:205–212, 1975.

*Primary Examiner*—Herbert J. Lilling
(74) *Attorney, Agent, or Firm*—Quarles & Brady LLP (57) ABSTRACT

An improved method for reducing colony forming units bacteria in yeast is disclosed. The method involves contacting the yeast with a hop acid in an amount sufficient to give a final concentration of the hop acid of at least about 40 ppm.

30 Claims, 6 Drawing Sheets

METHOD FOR DECONTAMINATING YEAST

CROSS-REFERENCE TO RELATED APPLICATIONS

This application claims priority to U.S. provisional application Ser. No. 60/130,591, filed Apr. 22, 1999.

STATEMENT REGARDING FEDERALLY SPONSORED RESEARCH OR DEVELOPMENT

Not applicable.

BACKGROUND OF THE INVENTION

Within the brewing industry, yeast used in a fermentation is commonly recovered from the fermentation and used again in several subsequent fermentations. It is imperative that the yeast remains free of bacterial contamination. One way of preventing bacterial contamination is to treat the yeast slurry to selectively eliminate bacteria (particularly beer spoilage lactic acid bacteria) under conditions that permit survival of the yeast cells. In one method, harvested brewers yeast is treated with acid to lower the pH to a point at which bacteria die and at which the yeast survive. Typically, inorganic acids (e.g., sulfuric or phosphoric acid) or organic acids (e.g., lactic acid) have been used for this disinfection process. However, our research has surprisingly shown that when the yeast has not been exposed to hop acids, as in the case of post fermentation hopping, acid disinfection is ineffective. This observation led to the unexpected discovery that hop acids (e.g., isohumulone) used in combination with phosphoric, sulfuric or lactic acid greatly increases the bactericidal effectiveness of the acid treatment.

However, there exist certain acid tolerant isolates of lactic acid bacteria such as Pediococcus and Lactobacillus species that are resistant to acid treatment, even when hop acids are present in harvested yeast taken from a kettle hopped fermentation or are added to yeast at concentrations typically found in kettle hopped fermentation.

Therefore, there exists a need in the art for a method of decontaminating yeast that is effective at reducing acid-resistant strains of lactic acid bacteria.

The present invention describes, inter alia, the use of an isomerized, reduced, and hydrogenated hop acid, tetrahydroiso-alpha acids (tetrahydroisohumulone, tetrahydroisocohumulone and tetrahydroadhumulone), in combination with organic and/or inorganic acid to disinfect brewer's (brink) yeast from all contaminant bacteria including acid resistant lactic acid bacteria. This combination is surprisingly more effective at killing lactic acid bacteria than inorganic or organic acids in combination with isohumulone (which is the primary alpha acid in kettle hopped beers) or in combination with reduced iso-alpha acids (dihydroiso-alpha acids). Tetrahydroiso-alpha acids are typically used as a post-fermentation hopping agent for adding bitterness and foam stability to beers and, as such, is not present in yeast harvested from fermentation. The addition of this compound at low concentrations to brink yeast prior to acid treatment has been shown to greatly increase the effectiveness of acid treatment for killing lactic acid bacteria. Raising the concentration to 40 ppm of tetrahydroiso-alpha acids in brink yeast is surprisingly very effective at killing even acid resistant bacteria. Furthermore, adding 40 ppm tetrahydroiso-alpha acids to brink yeast during storage and prior to acid treatment acts as a strong antimicrobial agent that reduces bacteria prior to acid treatment without having any appreciable effect on the yeast.

BRIEF SUMMARY OF THE INVENTION

The present invention is in part an improved method for reducing colony-forming units of bacteria in yeast comprising the steps of:

(a) contacting the yeast with a hop acid in an amount sufficient to give a final concentration of at least about 40 parts per million (ppm) when acid resistant bacterial strains are present or a final concentration at least 10 ppm when only non-acid resistant bacterial strains are present;

(b) holding the yeast mixture of step (a) for at least about five minutes;

(c) after step (b), adjusting the pH of the yeast mixture of step (b) to a pH in the range of from about 2.0 to about 2.6 with a suitable organic or inorganic acid; and (d) holding the yeast mixture of step (c) at a suitable temperature and for a period of time sufficient to reduce the bacterial colony forming units relative to a yeast slurry control treated with 20 ppm of iso-alpha acids.

It is an object of the invention to provide a method for reducing colony-forming units of bacteria in yeast.

It is an advantage of the invention that reduction of colony-forming units of bacteria in yeast may be accomplished by treating the yeast with a hop acid that is readily available.

It is a feature of the present invention that the method may be used to inhibit growth of bacteria in yeast while in storage, more particularly, the growth of beer spoilage lactic acid bacteria in brewer's yeast while in storage.

Other objects, features and advantages will become apparent upon review of the detailed description of the invention.

DESCRIPTION OF THE INVENTION

A number of hop acids in combination with inorganic acids or organic acids were evaluated for their ability to disinfect yeast seeded with an acid-resistant *Pediococcus damnosus* strain (the most acid-resistant encountered by us). Because *Pediococcus damnosus* is the most acid-resistant bacterium that we have encountered, it is reasonably expected that the methods of the present invention will not only be effective in disinfecting yeast contaminated with *Pediococcus damnosus,* and will also be effective in disinfecting yeast contaminated with other acid resistant and non-acid resistant bacteria.

Treatment of yeast with tetrahydroiso-alpha acids at a concentration of at least 40 ppm in combination with phosphoric acid at pH 2.3 was superior to other hop acid/inorganic acid combinations in reducing or eliminating the test Pediococcus microorganism. Treatment with tetrahydroiso-alpha acids at a lower concentration of 20 ppm, in conjunction with phosphoric acid, was shown to be inconsistent and ineffective at killing the acid-resistant Pediococcus. None of the other hop acids tested in this study performed as well as tetrahydroiso-alpha acids in combination with phosphoric acid. Tetrahydroiso-alpha acids preparations made from either beta or alpha acid fractions or by different manufacturers were shown to be equally effective. Also, the cis and trans isomers of tetrahydroiso-alpha acids were both shown to be equally effective. Using sulfuric acid in place of phosphoric acid and in combination with tetrahydroiso-alpha acids further increased the effectiveness of killing the test Pediococcus. Lactic acid and citric acid were equivalent to sulfuric acid when used at the same pH with tetrahydroiso-alpha acids. Compared to sulfuric or phosphoric acid, lactic acid and citric acid required much greater quantities of acid to bring the pH of the yeast slurry down to 2.3. Use of any of the test acids without hop acid addition was completely ineffective at killing the acid-resistant test Pediococcus.

Another method of disinfecting brewer's yeast is that of using acidified (with either phosphoric or sulfuric acid) ammonium persulfate (tested at 0.75% and 0.25% concentrations). In these studies it was also shown that the ability of acidified ammonium persulfate to kill the acid resistant test Pediococcus was also greatly enhanced by the addition of tetrahydroiso-alpha acids.

The pH of the yeast/hop acid mixture is preferably adjusted to a range from about 2.0 to about 2.6. More preferred is a pH range of about 2.2 to 2.4. It is reasonably expected that the invention is broadly applicable to the treatment of any yeast including, without limitation, ale yeast, wine yeast, distiller's yeast, baker's yeast, champagne yeast, cider-making yeast, food yeast, Kluveromyces yeast, etc.

It should also be understood that we reasonably expect that treating yeast with the hop acids of the present invention would be effective in reducing colony forming units of bacteria in such yeast during the interim that it is to be stored for future use. Such treatment of yeast with the hop acids of the present invention could be done by dosing the yeast with such hop acids before the yeast is dried for eventual shipment to the end user or by adding such hop acids to brink tank yeast slurries when it is anticipated that the brink tank yeast slurry will be held in the plant for a period of time before use in the plant. In such cases, we anticipate that a tetrahydroiso-alpha acid concentration of at least 40 ppm will provide effective bacterial control to the yeast.

Hop Acids Tested

The following purified hop acids, hop acid derivatives, and hop extracts were evaluated:

SPIRE B (reduced iso-alpha acids)—better known as dihydroiso-alpha acids (or rho-iso-alpha acids)

Redihop (reduced iso-alpha acids)—better known as dihydroiso-alpha acids (or rho-iso-alpha acids)

Alpha-Hydrohop—(alpha)-tetrahydroiso-alpha acids produced from alpha acids

Beta-Hydrohop—(beta)-tetrahydroiso-alpha acids produced from beta acids

Trans-tetrahydroiso-alpha acids

Cis-tetrahydroiso-alpha acids

Tetrahydroiso-alpha acids and iso-alpha acids (50:50 mixture)

Tetrahydro-alpha acids

Secondary iso-alpha acids (85% purity via secondary purification)

Hop character fraction (HCF)—hop oils

Hexahydroiso-alpha acids

Hexahydroiso-alpha acids and tetrahydroiso-alpha acids (50:50 mixture)

Hexahydrocolupulone

These purified hop acids, hop acid derivatives, and hop extracts are well known in the art and are available, for example, from Miller Brewing Company (Watertown Hops Company), John I. Haas, Inc., S. S. Steiner, Inc., and Kalsec (Kalamazoo Holdings, Inc.).

Bacterial Test Strains

Several isolates of acid-resistant Pediococcus species were obtained from yeast slurries from a brewery having problems with effectively disinfecting brewer's yeast. The most acid resistant isolate was selected and was identified by API's Rapid CHL, Biolog and a Qualicon Riboprinter as *Pediococcus damnosus.* One isolate lost its acid resistance on subculturing and was subsequently shown to have a riboprint pattern different from the acid resistant strain.

Brink Yeast Used for Disinfection Experiments

Brink yeast samples used in these studies were obtained from a commercial beer manufacturing facility. In all cases the yeast was harvested from fermentations that contained no hop acids. In each test the lowest generation yeast available was used.

Acid Disinfection Assay

Brink yeast samples were cooled to 34° F. with continuous stirring. Fresh isolates of the test Pediococcus strain were taken from BMB (Barney-Miller Brewery) agar (U.S. Pat. No. 4,906,573; Difco #T634-17) or Lactobacillus-MRS broth and were resuspended in sterile Lactobacillus MRS broth. This suspension was then added to the brink yeast sample and stirred for one hour to assure complete, uniform distribution of the bacteria. A sample of the seeded slurry was then taken and serially diluted in MRS broth and plated on BMB+ (BMB plus 3 ppm Actidione) agar to obtain 0-time control Pediococcus counts. 500-ml aliquots of the seed slurry were distributed into sterile one-liter beakers equipped with stir bars. Hop acids, inorganic acids and organic acids were added in different combinations to these slurries while measuring the pH using a calibrated pH meter. When hop acids were employed, the hop acids were added at least five minutes prior to the addition of the other acids.

All samples were then continually agitated using magnetic stirring at 34° F. for the specified time period. Samples were taken at one-hour intervals and were immediately pipetted into MRS broth to neutralize the pH and stop the acid treatment. These samples were then serially diluted in additional tubes of MRS broth. All dilutions were filter plated on BMB+ agar. All plates were than incubated in a $CO_2$ anaerobic incubator at 28° C. for seven days.

Experimental Results

Experiments were designed to determine whether modifying the yeast decontamination method of increasing the hop acid concentration or changing the inorganic acid would decrease the concentration of viable acid-resistant Fort Worth Pediococcus in yeast.

EXAMPLE 1

Figure 1:
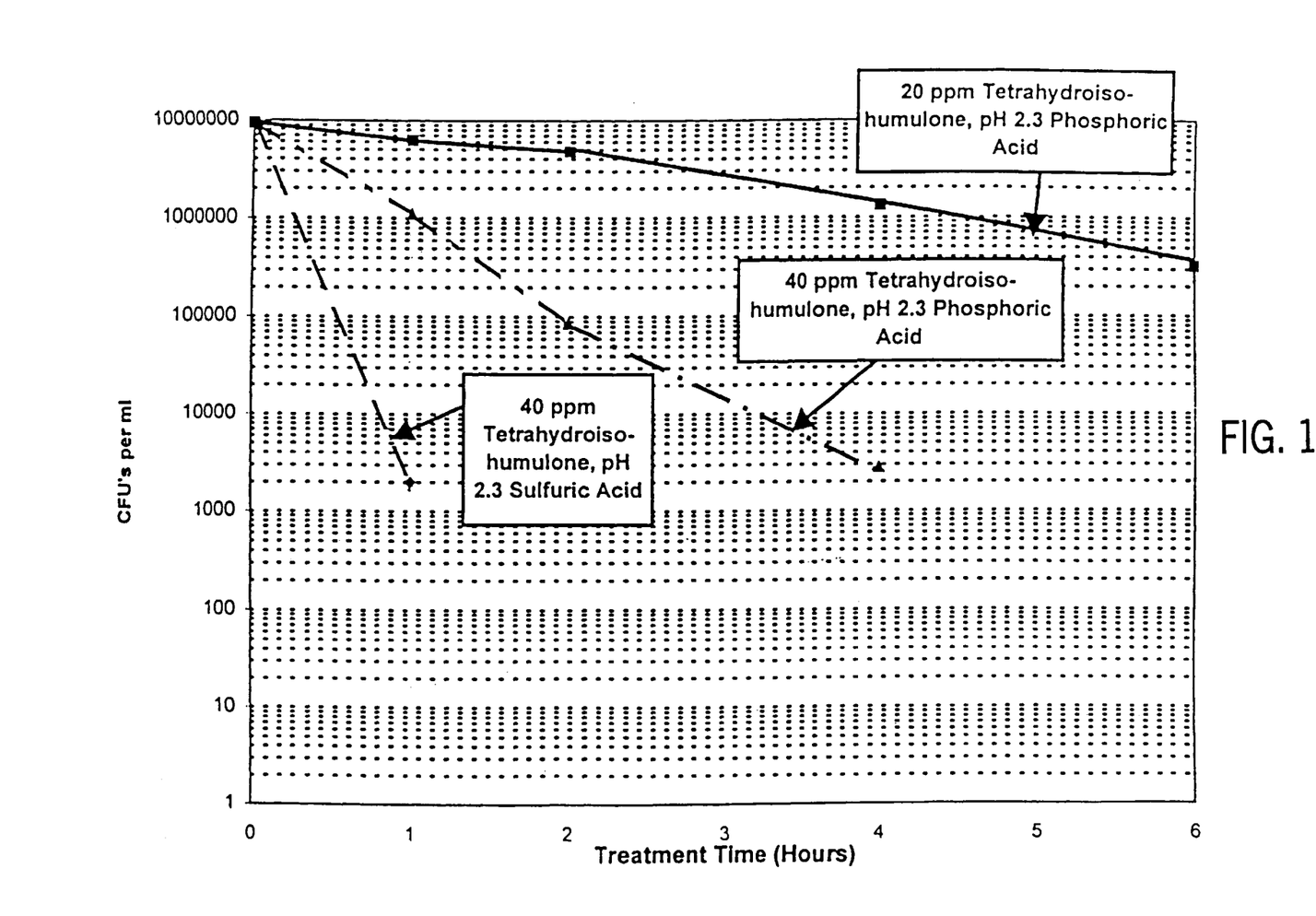
FIG. 1 shows the concentration of colony forming units (CFU's) of acid-resistant Pediococcus in yeast treated with tetrahydroisohumulone at two different concentrations in combination with phosphoric or sulfuric acid as a function of time.

FIG. 1 shows that increasing the tetrahydroiso-alpha acids (Hydrohop) concentration from 20 ppm to 40 ppm greatly improves the effectiveness of killing the test Pediococcus when using phosphoric acid treatment. The figure also shows that when sulfuric acid is used in place of phosphoric acid that the acid resistant Pediococcus is killed even more effectively.

EXAMPLE 2

Figure 2:
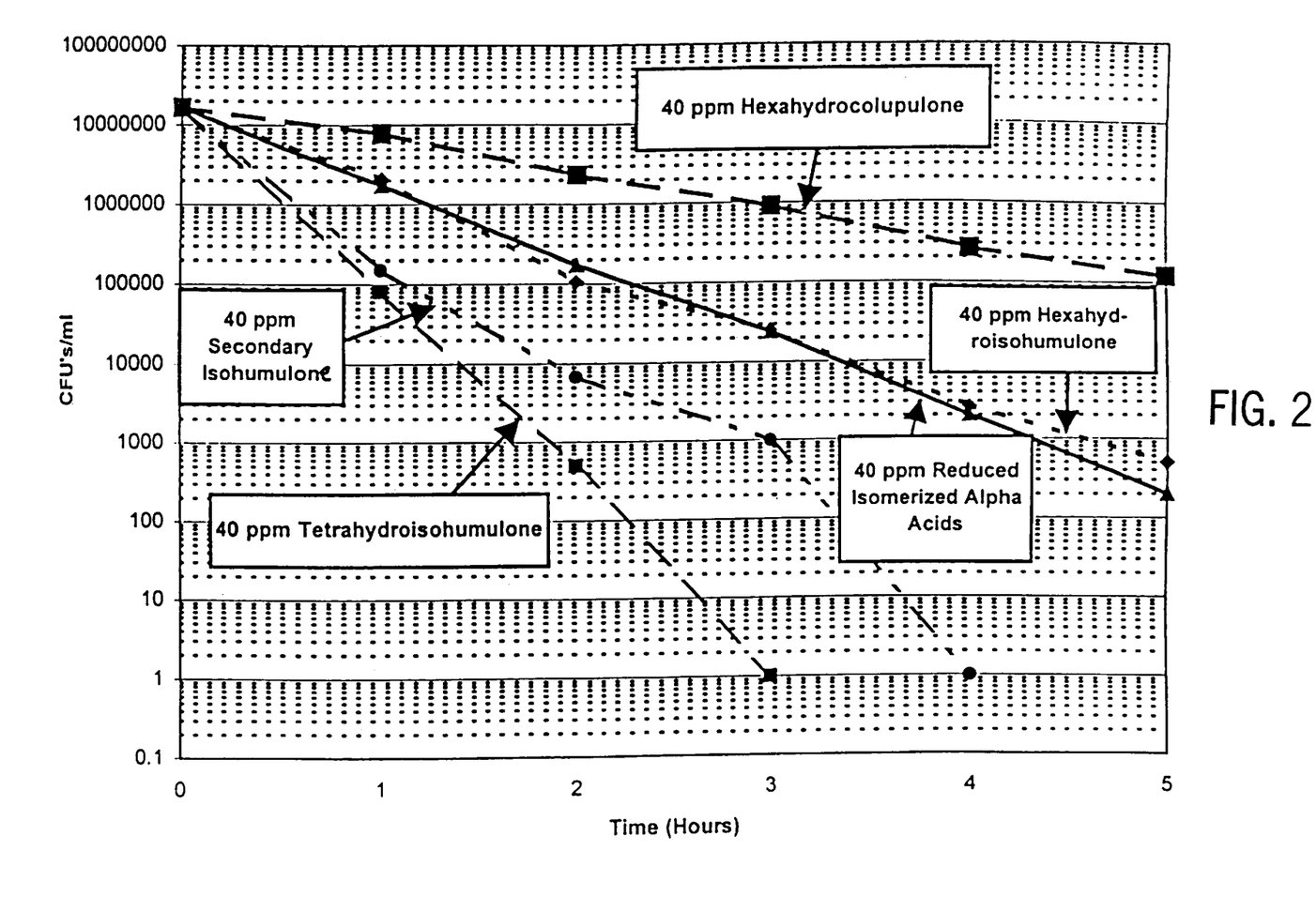
FIG. 2 shows the concentration of colony forming units of acid-resistant Pediococcus in yeast treated with various hop acids in combination with phosphoric acid as a function of time.

FIG. 2 presents data from an experiment comparing different hop acids (added at 40 ppm) in combination with phosphoric acid adjusted to pH for killing the acid resistant Pediococcus. As the graphs show, tetrahydroiso-alpha acids was superior to the four other hop acids tested. Hexahydrocolupulone, which in previous experiments was shown to be very efficient at killing other Gram positive bacteria, was the least effective at killing the test Pediococcus affording only two logs of kill in five hours. Reduced isomerized alpha acids and hexahydroiso-alpha acids were both effective at killing the test organism reducing the population 4 logs in five hours. However, they were still less effective than tetrahydroiso-alpha acids. Secondary iso-alpha acids were the second most effective (compared to tetrahydroiso-alpha acids) compound tested producing more than 6 logs of kill in 5 hours.

EXAMPLE 3

Figure 3:
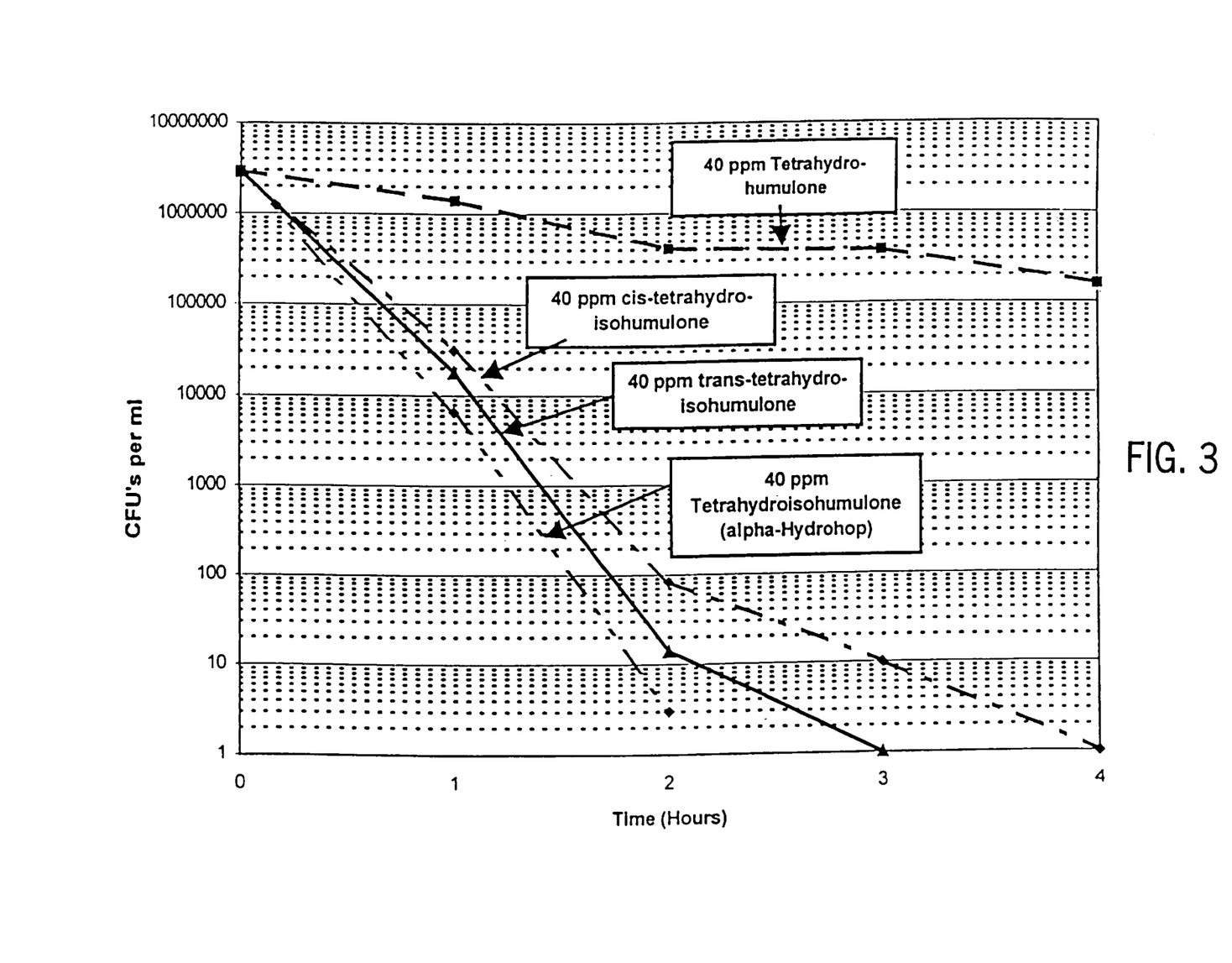
FIG. 3 shows the concentration of colony forming units of acid-resistant Pediococcus in yeast treated with various hop acids in combination with phosphoric acid as a function of time.

FIG. 3 graphs the data from an experiment comparing tetrahydroiso-alpha acids as well as cis-tetrahydroiso-alpha acids and trans-tetrahydroiso-alpha acids in combination to tetrahydroiso-alpha acids (formed from alpha acid) for disinfecting brewer's yeast seeded with an acid resistant Pediococcus. These were tested at a concentration of 40 ppm in combination with phosphoric acid and adjusting the pH to 2.3. As the graphs show, tetrahydro-alpha acids were ineffective at killing the acid resistant Pediococcus, showing only slightly more than one log of kill in five hours. The other three plots show that tetrahydroiso-alpha acids formed from alpha acids, cis-tetrahydroiso-alpha acids and trans-tetrahydroiso-alpha acids were closely equivalent to each other showing very good kill of the test organism. This demonstrated that there appears to be no difference in the cis and trans isomers for killing, and that tetrahydroiso-alpha acids produced from either beta (previous experiments) or alpha acids demonstrate the same effectiveness at killing the test organisms.

EXAMPLE 4

Figure 4:
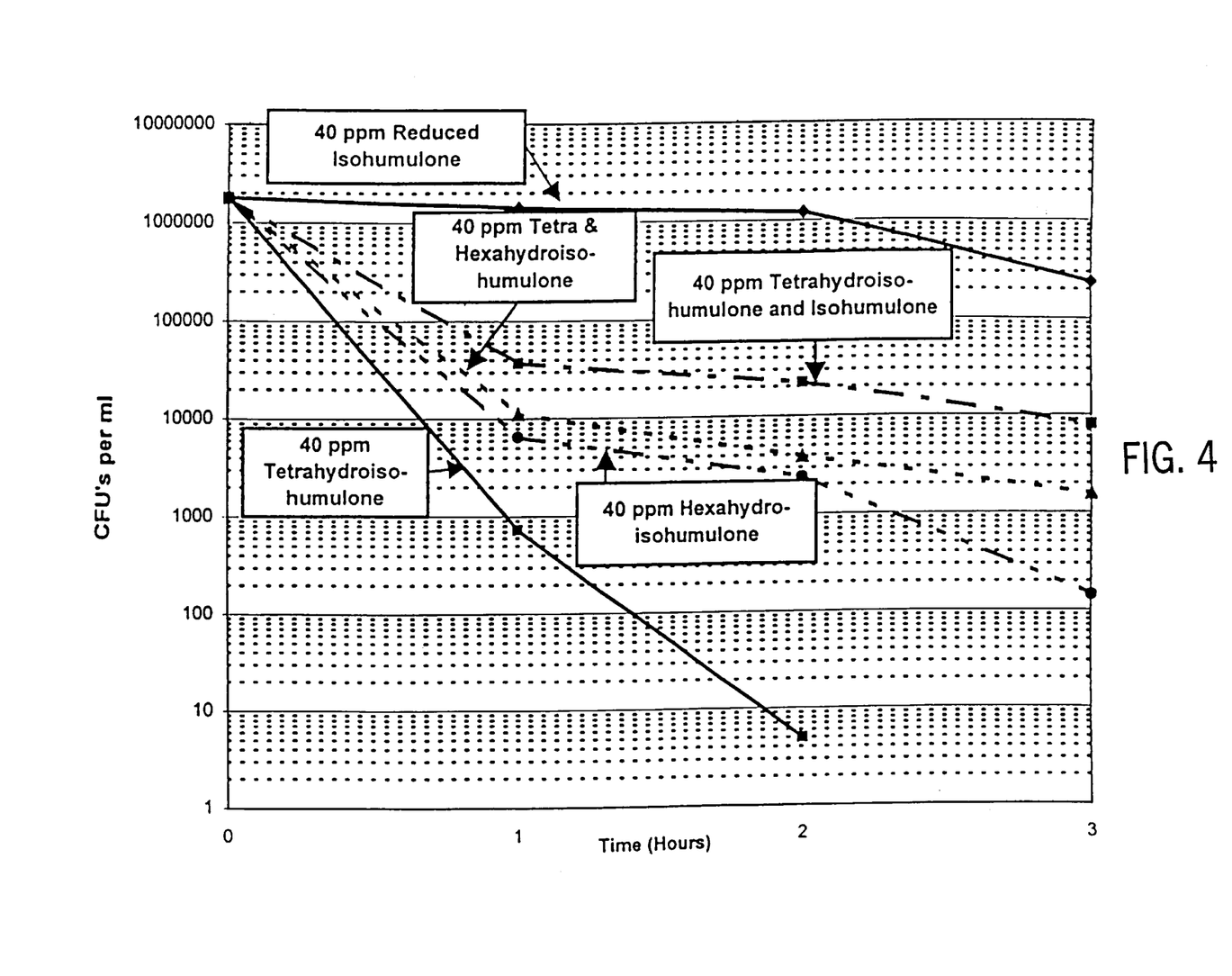
FIG. 4 shows the concentration of colony forming units of acid-resistant Pediococcus in yeast treated with various hop acids in combination with phosphoric acid as a function of time.

FIG. 4 shows a comparison of four other hop acids/hop acid mixtures compared to tetrahydroiso-alpha acids for disinfecting brewer's yeast seeded with an acid resistant Pediococcus. All were tested at a concentration of 40 ppm in combination with phosphoric acid adjusted to pH 2.3. Reduced isohumulone was very ineffective at killing the test bacterium. A commercial 50:50 mixture of tetrahydroiso-alpha acids and iso-alpha acids was more effective than the reduced iso-alpha acids. A commercial 50:50 mixture of tetrahydroiso-alpha acids and hexahydroiso-alpha acids and hexahydroiso-alpha acids alone were even more effective at killing the test organism during acid treatment. However, tetrahydroiso-alpha acids by themselves proved to be superior at killing the test organism.

EXAMPLE 5

Figure 5:
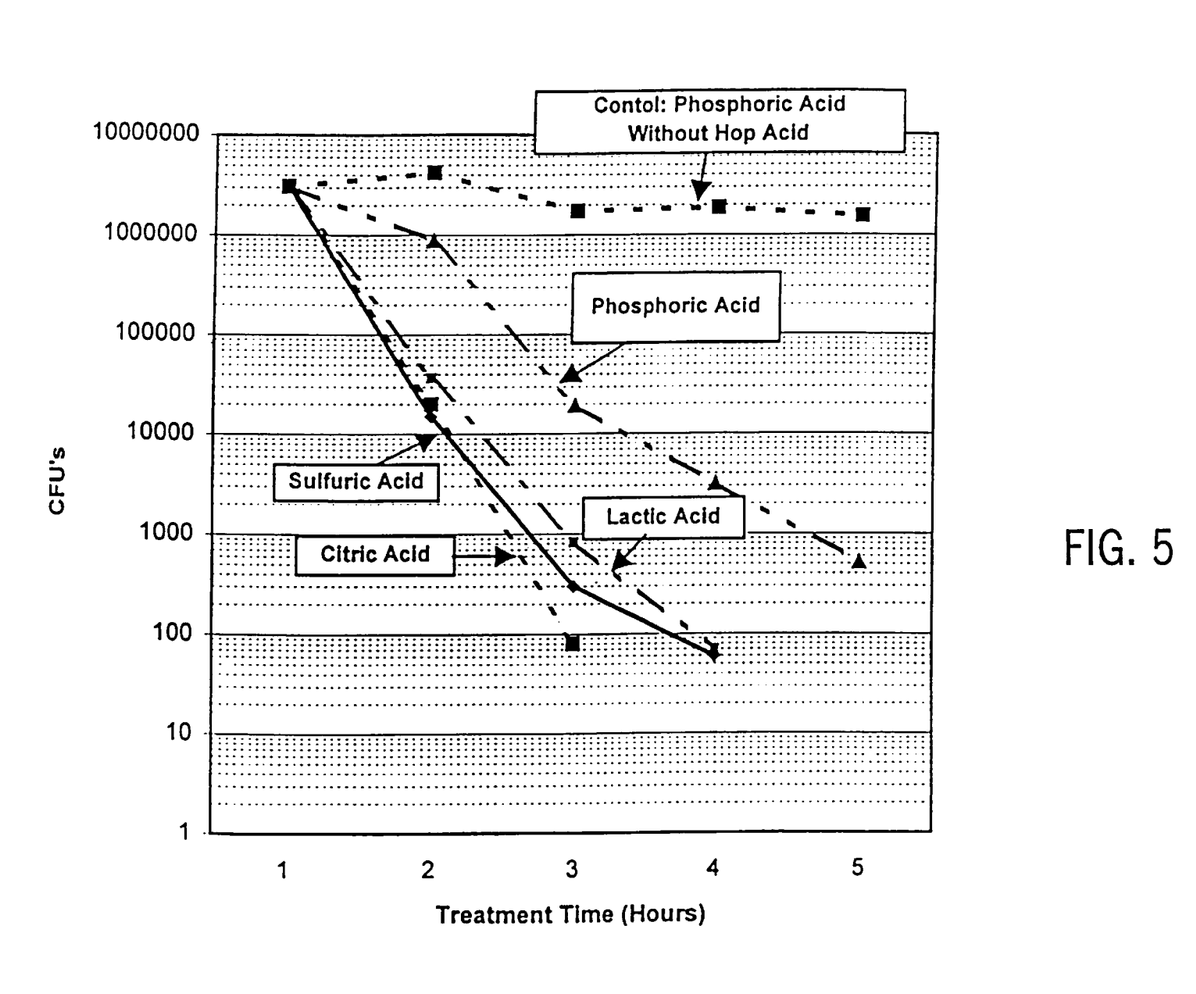
FIG. 5 shows the concentration of colony forming units of acid-resistant Pediococcus in yeast treated with tetrahydroisohumulone in combination with different inorganic or organic acids as a function of time.

FIG. 5 presents data from acid treatment of yeast seeded with an acid resistant Pediococcus using tetrahydroiso-alpha acids in combination with different inorganic and organic acids. The control of phosphoric acid with no hop acids added showed no kill of the test organism over five hours of treatment. When tetrahydroiso-alpha acids were added to phosphoric acid, the test organism was effectively killed. However, when sulfuric acid, lactic acid or citric acid were used to adjust the pH to 2.3 in combination with tetrahydroiso-alpha acids, the effectiveness of killing the test organism was increased further.

EXAMPLE 6

Figure 6:
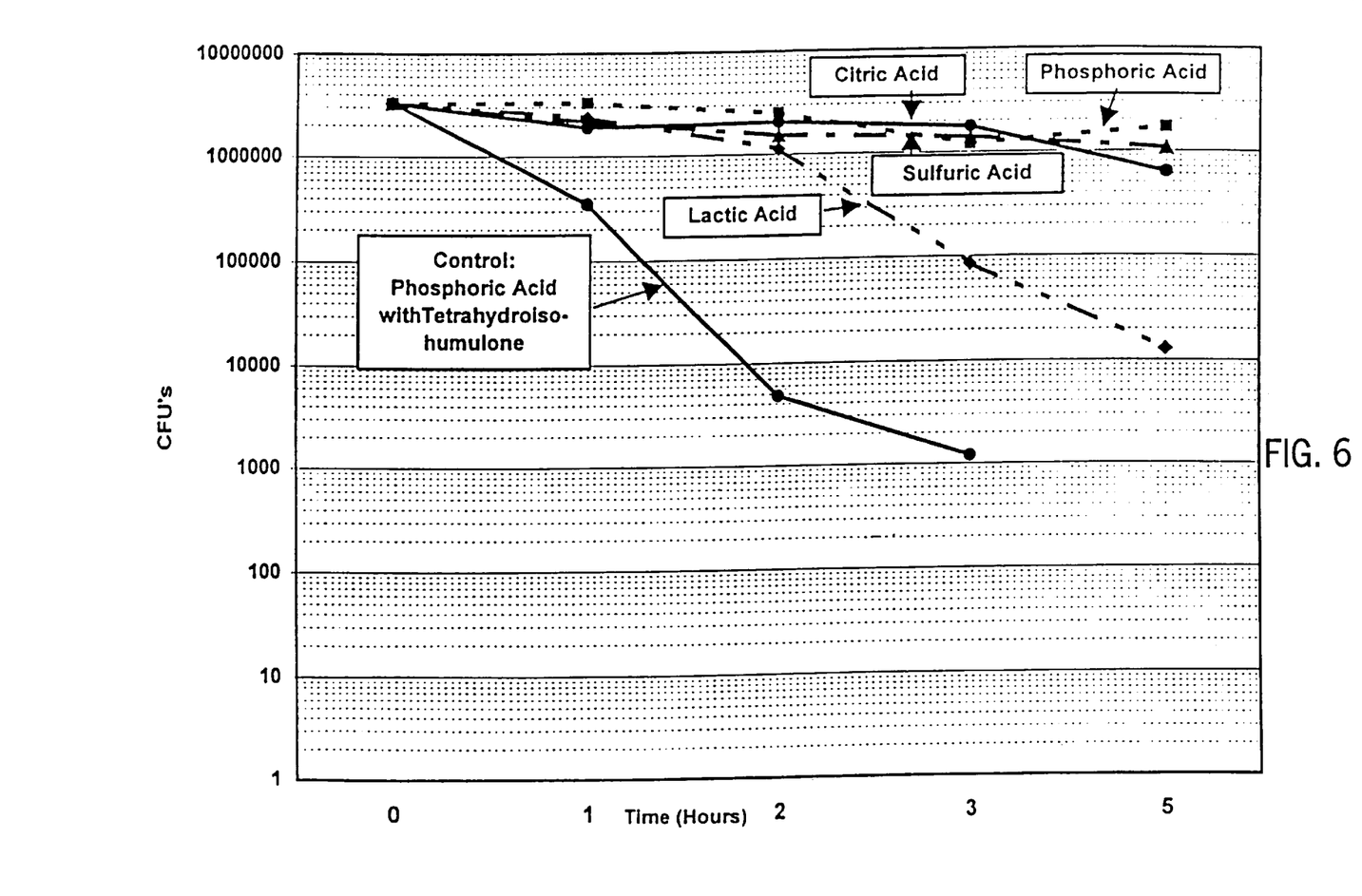
FIG. 6 shows the concentration of colony forming units of acid-resistant Pediococcus in yeast treated with different inorganic or organic acids without the presence of any hop acids and with tetrahydroisohumulone as a control.

FIG. 6 presents the data comparing citric acid, lactic acid, sulfuric acid and phosphoric acid at pH 2.3 without any hop acids added for killing the acid resistant Pediococcus in brewer's yeast. Only lactic acid showed some killing of the test organism after two hours of treatment. A control treated with 40 ppm tetrahydroiso-alpha acids and phosphoric acid showed effective kill over three hours of treatment.

Data from HCF (hop character fraction) is not presented here, but in previous experiments it was shown to have no antimicrobial effect against lactic acid bacteria.

We claim:

1. An improved method for reducing colony forming units of acid-resistant bacteria in yeast comprising the steps of:
   (a) contacting the yeast with a tetrahydroiso-alpha hop acid in an amount sufficient to give a final concentration of at least about 40 parts per million (ppm);
   (b) holding the yeast mixture of step (a) for at least about five minutes;
   (c) after step (b), adjusting the pH of the mixture of step (b) to from about 2.0 to about 2.6; and
   (d) holding the yeast mixture of step (c) at a suitable temperature and for a period of time sufficient to reduce the colony forming units relative to a yeast control treated with tetrahydroiso-alpha acids at a concentration of 20 ppm.

2. The method of claim 1, wherein the hop acid is selected from the group consisting of cis-tetrahydroiso-alpha acids, trans-tetrahydroiso-alpha acids, alpha-tetrahydroiso-alpha acids, beta-tetrahydroiso-alpha acids and combinations thereof.

3. The method of claim 1, wherein the pH is adjusted using an acid selected from the group consisting of sulfuric acid, phosphoric acid, citric acid, lactic acid, and combinations thereof.

4. The method of claim 1, wherein the acid resistant bacteria are Gram positive.

5. The method of claim 1, wherein the acid resistant bacteria are lactic acid bacteria.

6. The method of claim 1, wherein the acid resistant bacteria belong to the genus Pediococcus.

7. The method of claim 1, wherein the concentration of colony forming units is reduced at least about 100-fold relative to the concentration of colony forming units in yeast treated with 20 ppm tetrahydroiso-alpha hop acids.

8. The method of claim 1, wherein the slurry of step (d) is held at a suitable temperature for at least about 1 hour.

9. The method of claim 1, wherein the yeast is brewer's yeast.

10. The method of claim 1, wherein the pH is adjusted to from about 2.2 to about 2.4.

11. The method of claim 2, wherein the colony forming units are reduced by at least about 10-fold after one hour, relative to a control method in which the yeast is treated with 20 ppm of the corresponding tetrahydroiso-alpha acid.

12. An improved method for reducing colony forming units of bacteria in yeast to be stored comprising the step of:
(a) contacting the yeast to be stored with a tetrahydroiso-alpha acid in an amount sufficient to give a final concentration of at least about 40 parts per million (ppm).

13. The method of claim 12, comprising the additional step of (b) holding the yeast mixture of step (a) for at least about 5 minutes.

14. The method of claim 12, wherein the tetrahydroiso-alpha acid is selected from the group consisting of cis-tetrahydroiso-alpha acids, trans-tetrahydroiso-alpha acids, alpha-tetrahydroiso-alpha acids, beta-tetrahydroiso-alpha acids and combinations thereof.

15. The method of claim 12, wherein the yeast is brewer's yeast.

16. A yeast treated by the method of claim 1.

17. The yeast of claim 16, wherein the yeast is brewer's yeast.

18. A yeast treated by the method of claim 12.

19. The yeast of claim 18, wherein the yeast is brewer's yeast.

20. The method of claim 13, comprising the additional step of (c) adjusting the pH of the mixture of step (b) to from about 2.0 to about 2.6.

21. The method of claim 20, comprising the additional step of (d) holding the yeast mixture of step (c) at a suitable temperature and for a period of time sufficient to reduce the colony forming units relative to a yeast control treated with tetrahydroiso-alpha acids at a concentration of 20 ppm.

22. The method of claim 21, wherein the mixture of step (d) is held at a suitable temperature for at least about 1 hour.

23. The method of claim 20, wherein the pH is adjusted using an acid selected from the group consisting of sulfuric acid, phosphoric acid, citric acid, lactic acid, and combinations thereof.

24. The method of claim 20, wherein the pH is adjusted to from about 2.2 to about 2.4.

25. The method of claim 12, wherein the bacteria are acid-resistant bacteria.

26. The method of claim 25, wherein the bacteria are Gram positive.

27. The method of claim 25, wherein the bacteria are lactic acid bacteria.

28. The method of claim 25, wherein acid-resistant bacteria belong to the genus Pediococcus.

29. The method of claim 12, wherein the yeast is brewer's yeast.

30. The method of claim 21, wherein the colony forming units are reduced by at least about 10-fold after one hour, relative to a control method in which the yeast is treated with 20 ppm of the corresponding tetrahydroiso-alpha acid.

* * * * *